US005084476A

United States Patent [19]
Klaus et al.

[11] Patent Number: 5,084,476
[45] Date of Patent: Jan. 28, 1992

[54] TETRAHYDRONAPHTHALENE AND INDANE DERIVATIVES

[75] Inventors: Michael Klaus, Weil am Rhein; Ekkehard Weiss, Inzlingen, both of Fed. Rep. of Germany

[73] Assignee: Hoffmann-La Roche Inc., Nutley, N.J.

[21] Appl. No.: 395,005

[22] Filed: Aug. 17, 1989

Related U.S. Application Data

[62] Division of Ser. No. 72,075, Jul. 10, 1987, Pat. No. 4,876,349.

[51] Int. Cl.$^5$ .............................................. A61K 31/38
[52] U.S. Cl. ...................... 514/443; 549/29; 549/41; 549/43; 549/52; 549/57; 549/58
[58] Field of Search .............. 549/43, 41, 29, 52, 549/57, 58; 514/443

[56] References Cited

U.S. PATENT DOCUMENTS

| | | | |
|---|---|---|---|
| 4,174,405 | 11/1979 | Relyea et al. | 514/443 |
| 4,535,086 | 8/1985 | Klaus et al. | 514/337 |
| 4,578,498 | 3/1986 | Frickel et al. | 560/8 |
| 4,659,735 | 4/1987 | Klaus et al. | 514/443 |
| 4,680,291 | 7/1987 | Hamberger et al. | 549/29 |
| 4,742,077 | 5/1988 | Stütz | 514/443 |
| 4,760,174 | 7/1988 | Frickel et al. | 562/462 |
| 4,816,476 | 3/1989 | Klaus et al. | 514/443 |
| 4,876,349 | 10/1989 | Klaus et al. | 546/350 |

FOREIGN PATENT DOCUMENTS

| | | |
|---|---|---|
| 8547835 | 9/1984 | Australia. |
| 84667 | 8/1983 | European Pat. Off. . |
| 98591 | 1/1984 | European Pat. Off. . |
| 176032 | 4/1986 | European Pat. Off. . |
| 176033 | 4/1986 | European Pat. Off. . |
| 055314 | 5/1981 | Japan .................. 514/443 |

OTHER PUBLICATIONS

Derwent Abstract 86–089090/14.

Primary Examiner—Prince Willis, Jr.
Assistant Examiner—Ellen M. McAvoy
Attorney, Agent, or Firm—George M. Gould; George W. Johnston; Alan P. Kass

[57] ABSTRACT

The compounds of the formula

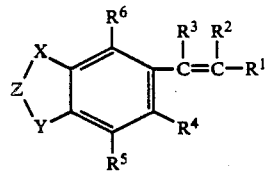

I wherein
X and Y are independently —$CH_2$— or >$C(CH_3)_2$; Z is —$CHR^8$—, >CO, >$CR^8OR^7$, —$CHR^8$—$CHR^8$—, —$CHOR^7$—$CH_2$—, —CO—$CHOR^7$ or —$CHOR^7$—$CHOR^7$—; $R^1$ is a 5- or 6-membered, monocyclic heterocyclic group which optionally can be C-substituted by halogen, lower-alkyl, lower-alkoxy, acyloxy, nitro, hydroxy, amino, lower-alkylamino or di-lower-alkylamino and/or which can be substituted on a ring —NH— group by lower-alkyl; $R^2$ and $R^3$ are independently hydrogen, lower-alkyl, trifluoromethyl or halogen and one of $R^2$ and $R^3$ always is trifluoromethyl or lower-alkyl; $R^4$ and $R^5$ are independently hydrogen, alkyl, alkoxy or halogen; $R^6$ is hydrogen, lower-alkyl or —$OR^7$; $R^7$ is hydrogen, lower-alkyl or acyl; $R^8$ is hydrogen or lower-alkyl; and $R^7$ and $R^8$ can be the same or different from one another, are useful for the treatment of neoplasms and dermatoses in mammals. The compounds can be manufactured from a corresponding bicyclic component and a heterocyclic component containing the residue $R^1$ by a Wittig, Horner or Grignard reaction and the optional subsequent transformation of reactive groups.

12 Claims, No Drawings

TETRAHYDRONAPHTHALENE AND INDANE DERIVATIVES

This is a division of application Ser. No. 07/072,075 filed July 10, 1987, now U.S. Pat. No. 4,876,349.

DESCRIPTION OF THE INVENTION

The present invention is concerned with tetrahydronaphthalene and indane derivatives of the formula

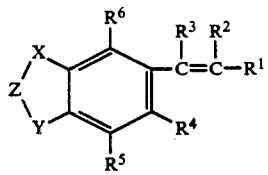

wherein
X and Y are independently —$CH_2$— or >$C(CH_3)_2$; Z is —$CHR^8$—, >CO, >$CR^8OR^7$, —$CHR^8$—$CHR^8$—, —$CHOR^7$—$CH_2$—, —CO—$CHOR^7$ or —$CHOR^7$—$CHOR^7$—; $R^1$ is a 5- or 6-membered, monocyclic heterocyclic group which is unsubstituted or can be C-substituted by halogen, lower-alkyl, lower-alkoxy, acyloxy, nitro, hydroxy, amino, lower-alkylamino or di-lower-alkylamino and/or which can be substituted on a ring —NH— group by lower-alkyl; $R^2$ and $R^3$ are independently hydrogen, lower-alkyl, trifluoromethyl or halogen and one of $R^2$ and $R^3$ is always trifluoromethyl or lower-alkyl; $R^4$ and $R^5$ are independently hydrogen, alkyl, alkoxy or halogen; $R^6$ is hydrogen, lower-alkyl or —$OR^7$; $R^7$ is hydrogen, lower-alkyl or acyl; $R^8$ is hydrogen or lower-alkyl; and $R^7$ and $R^8$ can be the same or different from one another.

The term "lower" is used throughout this description to refer to groups or substituents having 1 to 6 carbon atoms. Alkyl and alkoxy groups can be straight-chain or branched, such as methyl, ethyl, propyl, isopropyl, butyl, sec.-butyl and methoxy, ethoxy, propoxy, isopropoxy, butoxy and sec.-butoxy, respectively. Alkyl and alkoxy groups $R^4$ and $R^5$ preferably contain up to 10 carbon atoms such as octyl, nonyl, decyl and 2,2-dimethyloctyl and octyloxy, nonyloxy, decyloxy and 2,2-dimethyloctyloxy, respectively. Examples of the acyloxy groups are alkanoyloxy groups, preferably lower-alkanoyloxy groups such as acetoxy, propionyloxy, butyryloxy, pivaloyloxy and caproyloxy; or aroyloxy groups such as benzoyloxy, p-nitrobenzoyloxy and toluoyloxy; or aralkanoyloxy groups such as phenylacetoxy. Halogen embraces fluorine, chlorine, bromine and iodine. The heterocyclic group represented by $R^1$ can contain O, N and/or S as hereto atom(s). Examples include pyridyl, pyrimidinyl, furyl, thienyl, imidazolyl, isoxazolyl, oxazolyl and thiazolyl.

In greater detail, Examples of heterocylic group $R^1$ are pyridyl, especially 4-pyridyl; pyrimidinyl, especially 2- and 4-pyrimidinyl; thienyl; furyl; oxazolyl, especially 5-oxazolyl; isoxazolyl, especially 5-isoxazolyl; thiazolyl, especially 5-thiazolyl; pyrrolyl, especially 2-pyrrolyl; imidazolyl, especially 5-imidazolyl; and pyrazolyl, especially 5-pyrazolyl. As indicated, $R^1$ can be C-substituted by the aforementioned residues and/or can be substituted on a ring —NH— group by lower-alkyl, that is, the substituents can be present on one or more carbon atoms or on an NH group of the heterocyclic ring, with the substituent on an NH group being lower-alkyl. Examples of such substituted heterocyclic groups ($R^1$) are 3-substituted 4-pyridyl, 2,4-di-substituted 3-pyridyl, 1-substituted 2-pyrrolyl and 1,4-disubstituted imidazolyl.

The compounds of formula I can exist as trans or cis isomers or cis/trans isomer mixtures. In general, the trans compounds of formula I are preferred.

Among the compounds of formula I, preferred are those in which X and Y are >$C(CH_3)_2$ and Z represents —$CH_2$—$CH_2$—. $R^1$ is preferably an unsubstituted heterocyclic group. With respect to $R^2$ and $R^3$, hydrogen is preferred for $R^2$ and lower-alkyl especially methyl, is preferred for $R^3$. $R^4$ is preferably hydrogen or alkyl or alkoxy having up to 10 carbon atoms. $R^5$ and $R^6$ are preferably hydrogen.

The invention is also concerned in its other aspects with a process for the production of the compounds of formula I, pharmaceutical compositions based on the compounds of formula I and the use of the compounds of formula I in the treatment or prevention of neoplasms and dermatoses.

The compounds of formula I can be manufactured in accordance with the invention by reacting a compound of the formula

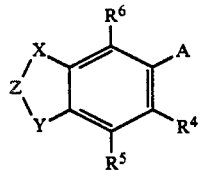

with a compound of the formula $R^1$—B in which
A is —$CH(R^3)P^+(Q)_3Y^-$ or —$CH(R^3)$—$P(O)(OAlk)_2$ and B is a residue $R^{21}$—CO—; or A is $R^{31}$—CO— and B is one of —$CH(R^2)P^+(Q)_3Y^-$, —$CH(R^2)$—$P(O)(OAlk)_2$ or —$CH(R^{21})MgHal$; or A is —$CH(R^{31})MgHal$ and B is $R^2$—CO—; Q is aryl; $Y^-$ is the anion of an organic or inorganic acid; Alk is a lower alkyl group; Hal is halogen; $R^{21}$ and $R^{31}$ are hydrogen, trifluoromethyl or lower-alkyl; and $R^1$, $R^2$, $R^3$, $R^4$, $R^5$, X, Y and Z have the meaning given above, If desired, a nitro group present as a substituent in $R^1$ is reduced to the amino group and, optionally, is mono- or di-alkylated, an acyloxy group $R^7$ or an acyloxy group present as a substituent in $R^1$ is saponified, a carbonyl group present in Z is reduced to the hydroxy group, and a hydroxy group $R^7$ or a hydroxy group present as a substituent in $R^1$ or present in Z is alkylated or acylated.

The reaction of the compounds of formula II and $R^1$—B can be carried out according to the known methods of the Wittig, Horner or Grignard reaction.

In the case of the Wittig reaction, i.e. with the use of a compound of formula II with A being —$CH(R^3)P^+(Q)_3Y^-$ or of the formula $R^1$—B with B being —$CH(R^2)P^+(Q)_3Y^-$, the components are reacted with one another in the Presence of an acid-binding agent, for example, a strong base such as butyllithium, sodium hydride or the sodium salt of dimethyl sulphoxide, and especially in the Presence of an optionally lower alkyl-substituted ethylene oxide such as 1,2-butylene oxide. A reaction solvent is optional, for example, an ether such as diethyl ether or tetrahydrofuran or in an aromatic hydrocarbon such as benzene. The reaction is conducted at a temperature between room temperature and the boiling point of the reaction mixture.

Among the inorganic acid ions $Y^-$ the chloride ion, the bromide ion or the hydrosulphate ion is preferred, and among the organic acid ions the tosyloxy ion is preferred. The aryl group Q is preferably phenyl or a substituted phenyl such as p-tolyl.

In the case of the Horner reaction, that is, with the use of a compound of formula II with A being —CH($R^3$)—P(O)(OAlk)$_2$ or of the formula $R^1$—B with B being —CH($R^2$)—P(O)(OAlk)$_2$, the components are condensed with the aid of a base and Preferably in the presence of an inert organic solvent, for example, with the aid of sodium hydride in benzene, toluene, dimethylformamide, tetrahydrofuran, dioxane or 1,2-dimethoxyethane, or also with the aid of a sodium alcoholate in an alkanol, for example, sodium methylate in methanol, at a temperature between 0° and the boiling point of the reaction mixture.

The alkoxy groups OAlk are especially lower alkoxy with 1-6 carbon atoms such as methoxy or ethoxy.

The reaction of a compound of formula II, with A being —CH($R^{31}$)MgHal, or of the formula $R^1$—B, with B being —CH($R^{21}$)MgHal, can be carried out in a manner known per se under the conditions of a Grignard reaction, for example, in an ether such as diethyl ether or tetrahydrofuran at room temperature and subsequent water-cleavage with acidic agents, for example, with organic acids such as p-toluenesulphonic acid.

Compounds of formula I which contain an amino substituent in the heterocyclic ring are conveniently prepared via the corresponding nitro compounds. A nitro group Present in a compound of formula I can be converted into an amino group in a manner known per se by reduction, for instance, with nascent hydrogen. An amino group Present in a compound of formula I can be mono- or di-alkylated in a manner known per se, for example, by treatment with alkylating agents such as alkyl halides or alkyl sulphates or by reductive alkylation with aldehydes such as formaldehyde or acetaldehyde and sodium cyanoborohydride. The reduction of a carbonyl group Present in Z as well as the alkylation and acylation of hydroxy groups can also be carried out in a manner known per se. For example, a carbonyl group can be reduced to the hydroxy group by treatment with reduction agent such as sodium borohydride.

As indicated, the compounds of formula I can exist in trans or cis form. In the Process described above they are mainly obtained in the trans form. Cis components which may be obtained can be separated, if desired, in a manner known per se.

The starting materials of formula II and $R^1$—B, insofar as their preparation is not known or is not described hereinafter, can be prepared in analogy to known methods or to methods described hereinafter.

The compounds of formula I are therapeutically active. In particular, they possess anti-seborrhoeic, anti-keratinizing, anti-neoplastic and anti-allergic/anti-inflammatory activity, which can be demonstrated using the test procedures described hereinafter: A) The anti-keratinizing activity can be determined on the rhino mouse model according to the following Procedure. The skin of the rhino mouse is characterized by the Presence of keratin-filled utriculi of the epidermis and subcutaneous cysts, both of which are derived from hair follicles. The administration of retinoids leads to a hyperproliferation of the epidermis and of the epithelium lining of the utriculi. The thickening of the epidermis and the reduction in the size of the utriculi lead to a normalization of the altered structure of the epithelium layer. The daily topical application, to the skin of the rhino mouse, of a 3% acetone solution of an active test compound in an amount of 0.1 ml/cm$^2$ over a period of 3 weeks, or the thrice weekly oral administration of the active test compound in arachis oil over a Period of 3 weeks, leads to a significant proliferation of the epidermis and a striking reduction of the keratin-filled utriculi. B) The activity in the Prevention of chemically-induced breast tumors can be determined according to the following Procedure. Female Sprague-Dawley rats are kept under temperature-controlled and light-controlled conditions, with free access to drinking water and feed. At the age of 50 days 15 mg of dimethylbenz(a)anthracene dissolved in arachis oil are administered to each rat by means of a probang. The treatment with the test compounds begins 1 day after the administration of the carcinogen. The body weights of the test animals are recorded and the tumors are palpated weekly and measured with a vernier caliper. The volumes are calculated according to the formula D/2·d$^2$ in which D represents the larger diameter of the tumor ellipsoid and d represents the smaller diameter of the tumor ellipsoid. After 11 weeks the test is terminated and evaluated. In this test there are used in addition to 30 control animals, which receive exclusively normal feed, the following two groups of rest animals:

1. 33 rats to which are administered daily 30 mg/kg of test compound mixed with the feed; and 2. 36 rats to which are administered daily 90 mg/kg of test compound mixed with the feed. C) The activity on tumors can be determined on the transplantable chondrosarcoma of the rat according to the following method. The solid tumor of a donor animal is finely minced and suspended in phosphate buffer/ sodium chloride solution. Thereafter 0.5 ml of the 30% tumor suspension is implanted subcutaneously into albino rats.

The transplanted rats are divided into test groups of 8 animals each. The test compounds are suspended in arachis oil and administered orally five times per week for 24 days. The tumors are excised and weighed on day 24. The results are expressed in the quotient C/T which is calculated as follows:

$$C/T = \frac{\text{Average tumor weight of control}}{\text{Average tumor weight of treated}}$$

D) The antimetaplastic activity can also be determined in rats according to the following method. Female Holtzmann rats weighing approximately 100 g are ovarectomized under Thiogenal narcosis after an adaptation Period of 8 days and are used in the test after a further 14 days. In each case two animals are Placed in a cage with free access to feed which contains approximately 2000 IU of vitamin A determined analytically. Prior to the oral administration of the test compound the animals are treated subcutaneously each day on 6 successive days with 1 $\mu$g of estradiol benzoate and 250 $\mu$g of testosterone propionate dissolved in 0.1 ml of sesame oil. The parenteral hormone administration leads to the formation of a clear granular stage in the vaginal smear, that is, a squamous, metaplasia. Two days after the oral administration of the test substance the result of the reaction is again read off on the vaginal epithelium. The area method according to Behrens and Karber is employed to calculate the average effective dosages.

E) The activity of the compounds I on sebum secretion in rats was determined according to the following procedure. Male rats of approximately 50-60 g body weight were castrated at the age of 21-22 days. One week after this operation the rats were washed in a cleansing solution in order to remove sebum which was excreted prior to the test period. Only the carrier materials used were administered to one group of rats. A further group of rats also simultaneously received 100 μg of testosterone propionate in 0.2 ml of sesame oil per rat per day. To a further group of rats there were administered daily Per rat 100 μg of testosterone propionate in 0.2 ml of sesame oil subcutaneously and the test compounds in various dosages in 0.2 ml of propylene glycol orally. The rats were treated in this manner for 14 days. On the 15th day the sebum from the skin surface and the pelt was removed by immersing the entire body of the test animals in a determined volume of acetone and bathing therein for 2 minutes. An aliquot of the solvent bath was evaporated and the solid residue was determined, gravimetrically. The inhibition of the testosterone-stimulated increase in the serum secretion in comparison to the corresponding values from rats treated only with testosterone propionate was used as the measurement for the activity.

The compounds of formula I are useful in mammals for the topical and systemic therapy of benign and malignant neoplasms, of premalignant lesions and also for the systemic and topical prophylaxis of the said conditions.

Furthermore, they are useful in mammals for the topical and systemic therapy of acne, psoriasis and other dermatoses which are accompanied by an intensified or pathologically altered conification, as well as of inflammatory and allergic dermatological conditions. Further, the compounds of formula I can also be used for the control of mucous membrane disorders with inflammatory or-degenerative or metaplastic changes in such species.

The pharmaceutical preparations can be administered enterally, parenterally or topically. Suitable for enteral administration are preparations in the form of tablets, capsules, dragees, syrups, suspensions, solutions and suppositories. preparations in the form of infusion of injection solutions are suitable for Parenteral administration.

The dosages in which the preparations are administered can vary according to the mode of use and route of use as well as according to the requirements of the patients. In general, daily doses of about 0.1-50 mg/kg, preferably 1-15 mg/kg, are suitable adults.

The preparations can be administered in one dosage or several dosages. Capsules containing about 5-200 mg of active substance are a preferred form.

The preparations can contain inert or pharmacodynamically active additives. Tablets or granulates can contain a series of binding agents, filler materials, carrier substances or diluents. Liquid preparations can be present, for example, in the form of the sterile solution which is miscible with water. Capsules can contain a filler material or thickening agent in addition to the active substance. Furthermore, flavor-improving additives as well as the substances usually used as preserving, stabilizing, moisture-retaining and emulsifying agents, salts for varying the osmotic pressure, buffers and other additives can also be present.

The previously mentioned carrier substances and diluents can be organic or inorganic substances, for example, water, gelatin, lactose, starch, magnesium stearate, talc, gum arabic, polyalkylene glycols, and the like. It is a prerequisite that all adjuvants used in the Production of the preparations be non-toxic.

For topical use the active substances are conveniently used in the form of salves, tinctures, creams, solutions, lotions, sprays, suspensions and the like. Salves and creams as well as solutions are preferred. These preparations intended for topical use can be manufactured by mixing the compounds of formula I as active ingredients with non-toxic, inert, solid or liquid carriers which are conventional for such preparations and which are suitable for topical treatment.

Suitable for topical use are solutions containing 0.1-5%, preferably 0.3-2%, of the active substance and salves or creams containing 0.1-5%, preferably about 0.2-2%, of the active substance.

If desired, the pharmaceutical preparations can contain an antioxidant, for example, tocopherol, N-methyl-γ-tocopheramine, butylated hydroxyanisole or butylated hydroxytoluene.

The following Example illustrates the preparation of a compound of the invention further. The temperatures are given in degrees Celsius.

EXAMPLE 378 g of [1-(5,6,7,8-tetrahydro-5,5,8,8-tetramethyl-2-naphthyl)ethyl]triphenylphosphonium bromide were suspended in 4 l of butylene oxide. After the addition of 51 ml of 4-pyridinecarbaldehyde the mixture was boiled at reflux for 1.5 hours. After cooling the majority of the solvent was evaporated in a water-jet vacuum, the residue was poured into 1.5 l of a methanol/water mixture (ratio 6:4) and extracted repeatedly with hexane. The organic phase was washed three times with water and, after drying over sodium sulphate, evaporated. After flash chromatography (eluting agent hexane/ether=2:1) and recrystallization from hexane there were obtained 216 g of 4-[(E)-2-(5,6,7,8-tetrahydro-5,5,8,8,-tetramethyl-2-naphthyl) propenyl]pyridine in colorless crystals, melting point 84–85°.

Analogously there were obtained the following additional compounds in accordance with the present invention:

3-[(E)-2-(5,6,7,8-tetrahydro-5,5,8,8-tetramethyl-2-napthyl) propenyl]pyridine, melting point 93-95°, 2-[(E)-2-(5,6,7,8-tetrahydro-5,5,8,8-tetramethyl-2-naphthyl) propenyl]pyridine, melting point 77°-79°, 2-[(E)-2-(5,6,7,8-tetrahydro-5,5,8,8-tetramethyl-2-naphthyl) propenyl]thiophene, melting point 52°-54°, 3-[(E)-2-(5,6,7,8-tetrahydro-5,5,8,8-tetramethyl-2-naphthyl) propenyl]thiophene, melting point 80°-82°, 2-[(E)-2-(5,6,7,8-tetrahydro, 5,5,8,8,-tetramethyl-2-naphthyl) propenyl]furan, melting point 52°-54°.

4-[(E)-2-(5,6,7,8-tetrahydro-5,5,8,8-tetramethyl-2-naphthyl) propenyl]pyrimidine, melting point 114°.

We claim:

1. A compound of the formula

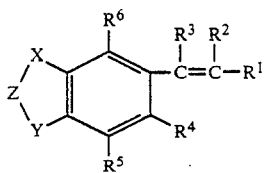

wherein
X and Y are independently —CH$_2$— or >(CH$_3$)$_2$; Z is —CHR$^8$—, or —CHR$^8$—CHR$^8$-; R$^1$ is thienyl which is unsubstituted or can be C-substituted by halogen, lower-alkyl, lower-alkoxy, acyloxy, nitro, hydroxy, amino, lower-alkylamino or di-lower-alkylamino; R$^2$ and R$^3$ are independently hydrogen, lower-alkyl, trifluoromethyl or halogen and one of R$^2$ and R$^3$ is always trifluoromethyl or lower-alkyl; R$^4$ and R$^5$ are independently hydrogen, alkyl, alkoxy or halogen; R$^6$ is hydrogen, lower-alkyl or a residue —OR$^7$; R$^7$ is hydrogen, lower-alkyl or acyl; R$^8$ is hydrogen or lower-alkyl; and R$^7$ and R$^8$ can be the same or different from one another.

2. The compound in accordance with claim 1 in which X and Y are >C(CH$_3$)$_2$; Z is —CH$_2$—CH$_2$—; R$^1$ is unsubstituted thienyl; R$^2$, R$^5$ and R$^6$ are hydrogen; and R$^4$ is hydrogen and alkyl or alkoxy having up to 10 carbon atoms.

3. The compound of claim 2, 3-[(E)-2-(5,6,7,8-tetrahydro-5,5, 8,8-tetramethyl-2-naphthyl)propenyl]thiophene.

4. The compound of claim 1, 2-[(E)-2-(5,6, 7,8-tetrahydro-5,5,8,8-tetramethyl-2-naphthyl)propenyl]thiophene.

5. A process for producing a compound of the formula:

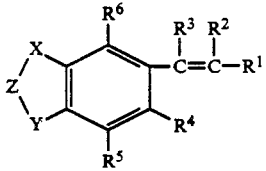

wherein
X and Y are independently —CH$_2$— or >C(CH$_3$)$_2$; Z is —CHR$^8$—, [>CO, >CR$^8$OR$^7$,] or —CHR$^8$—CHR$^8$-[, —CHOR$^7$—CH$_2$—, —CO—CHOR$^7$ or —CHOR$^7$—CHOR$^2$—]; R$^1$ is [a 5- or 6-membered, monocyclic heterocyclic group] thienyl which is unsubstituted or can be C-substituted by halogen, lower-alkyl, lower-alkoxy, acyloxy, nitro, hydroxy, amino, lower-alkylamino or di-lower-alkylamino; R$^2$ and R$^3$ are independently hydrogen, lower-alkyl, trifluoromethyl or halogen and one of R$^2$ and R$^3$ is always trifluoromethyl or lower-alkyl; R$^4$ and R$^5$ are independently hydrogen, alkyl, alkoxy or halogen; R$^6$ is hydrogen, lower-alkyl or a residue —OR$^7$; R$^7$ is hydrogen, lower-alkyl or acyl; R$^8$ is hydrogen or lower-alkyl; and R$^7$ and R$^8$ can be the same or different from one another, which process comprises reacting a compound of the formula

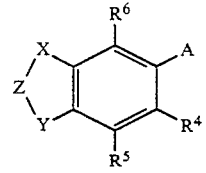

with a compound of the formula

R$^1$—B in which
A is —CH(R$^3$)P$^+$(Q)$_3$Y$^-$ or —CH(R$^3$)—P(O)-(OAlk)$_2$ and B is R$^{21}$—CO—; or
A is R$^{31}$—CO— and B is one of —CH(R$^2$)P$^+$(Q)$_3$Y$^-$ or —CH(R$^2$)—P(O)(OAlk)$_2$ or —CH(R$^{21}$)MgHal; or
A is —CH(R$^{31}$)MgHal and B is R$^2$—CO—; Q is aryl; Y$^-$ is the anion of an organic or inorganic acid; Alk is a lower alkyl group; Hal is halogen; R$^{21}$ and R$^{31}$ are hydrogen, trifluoromethyl or lower-alkyl; and R$^1$, R$^2$, R$^3$, R$^4$, R$^5$, X, Y and Z have the same meanings as above.

6. The process in accordance with claim 5 in which X and Y are >C(CH$_2$)$_2$; Z is —CH$_2$—CH$_2$—; R$^1$ is unsubstituted thienyl; R$^2$, R$^5$, and R$^6$ are hydrogen; and R$^4$ is hydrogen or alkyl or alkoxy having up to 10 carbon atoms.

7. A pharmaceutical composition comprising as the active substance a compound of the formula

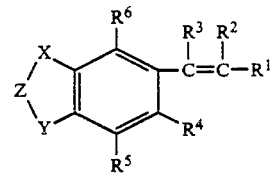

wherein
X and Y are independently —CH$_2$— or >C(CH$_3$)$_2$; Z is —CHR$^8$—, [>CO, >CR$^8$OR$^7$,] or —CHR$^8$—CHR$^8$-[, —CHOR$^7$—CH$_2$—, —CO—CHOR$^7$ or —CHOR$^7$—CHOR$^7$]; R$^1$ is thienyl which is unsubstituted or can be C-substituted by halogen, lower-alkyl, lower-alkoxy, acyloxy, nitro, hydroxy, amino, lower-alkylamino or di-lower-alkylamino; R$^2$ and R$^3$ are independently hydrogen, lower-alkyl, trifluoromethyl or halogen and one of R$^2$ and R$^3$ is always trifluoromethyl or lower-alkyl; R$^4$ and R$^5$ are independently hydrogen, alkyl, alkoxy, or halogen, R$^6$ is hydrogen, lower-alkyl or a residue —OR$^7$; R$^7$ is hydrogen, lower-alkyl or acyl; R$^8$ is hydrogen or lower-alkyl; and R$^7$ and R$^8$ can be the same or different from one another, and a pharmaceutically acceptable carrier.

8. The composition in accordance with claim 7, in which for the compound of formula I, X and Y are >C(CH$_3$)$_2$; Z is —CH$_2$—CH$_2$—; R$^1$ is unsubstituted thienyl; R$^2$, R$^5$ and R$^6$ are hydrogen; and R$^4$ is hydrogen or alkyl or alkoxy having up to 10 carbon atoms.

9. The composition of claim 7, wherein the compound of formula I is selected from the group consisting of 2-[(E)-2-(5,6,7,8-tetrahydro-5,5,8,8-tetramethyl-2-naphthyl) propenyl]thiopene and 3-[(E)-2-(5,6,7,8-tetrahydro-5,5,8,8-tetramethyl-2-naphthyl) propenyl]thiopene.

10. A method for treating neoplasms and dermatose in mammals which comprises administering an effective amount of a pharmaceutical composition containing a compound of the formula;

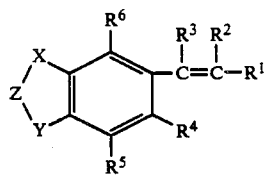

I wherein

X and Y are independently —CH$_2$— or >C(CH$_3$)$_2$; Z is —CHR$^8$—, [>CO, >CR$^8$OR$^7$,] or —CHR$^8$—CHR$^8$-[, —CHOR$^7$—CH$_2$—, —CO—CHOR$^7$ or —CHOR$^7$—CHOR$^7$—]; R$^1$ is thienyl which is unsubstituted or can be C-substituted by halogen, lower-alkyl, lower-alkoxy, acyloxy, nitro, hydroxy, amino, lower-alkylamino or di-lower-alkylamino; R$^2$ and R$^3$ are independently hydrogen, lower-alkyl, trifluoromethyl or halogen and one of R$^2$ and R$^3$ is always trifluoromethyl or lower-alkyl; R$^4$ and R$^6$ are independently hydrogen, alkyl, alkoxy, or halogen; R$^6$ is hydrogen, lower-alkyl, or a residue —OR$^7$; R$^7$ is hydrogen, lower-alkyl or acyl, R$^8$ is hydrogen or lower-alkyl; and R$^7$ and R$^8$ can be the same or different from one another, and a pharmaceutically acceptable carrier.

11. The method in accordance with claim 10, in which for the compound of formula I, X and Y are >C(CH$_3$)$_2$; Z is —CH$_2$—CH$_2$—; R$^1$ is unsubstituted thienyl; R$^2$, R$^5$ and R$^6$ are hydrogen; and R$^4$ is hydrogen or alkyl or alkoxy having up to 10 carbon atoms.

12. The method of claim 10, wherein the compound employed is selected from the group consisting of 2-[(E)-2-(5,6,7,8-tetrahydro-5,5, 8,8-tetramethyl-2-naphthyl)propenyl]thiophene and 3-[(E)-2-(5,6,7,8-tetrahydro-5,5,8,8-tetramethyl-2-naphthyl) propenyl]thiopene.

* * * * *

UNITED STATES PATENT AND TRADEMARK OFFICE
CERTIFICATE OF CORRECTION

PATENT NO. : 5,084,476                                    Page 1 of 2
DATED      : January 28, 1992
INVENTOR(S): Michael Klaus and Ekkehard Weiss It is certified that error appears in the above-identified patent and that said Letters Patent is hereby corrected as shown below:

Between the title Related U.S. Application Data and [51] Int. Cl.$^5$, please insert the following:

[30]  Foreign Application Priority Data

July 15, 1986    [CH]  Switzerland    2826/86

In The Claims:

In claim 1, column 7, line 11, change ">(CH$_3$)$_2$" to -- >C(CH$_3$)$_2$ --;

In claim 2, column 7, line 29, change "hydrogen and alkyl" to -- hydrogen or alkyl --;

In claim 5, column 7, line 49, change ">(CH$_3$)$_2$" to -- >C(CH$_3$)$_2$ --;

In claim 5, column 7, line 50, delete "[>CO, >CR$^8$OR$^7$,]";

In claim 5, column 7, lines 51-52, delete "[, -CHOR$^7$-CH$_2$-, -CO-CHOR$^7$ or -CHOR$^7$-CHOR$^2$-]";

In claim 5, column 7, lines 52-53, delete "[a 5- or 6-membered, monocyclic heterocyclic group]";

In claim 6, column 8, line 27, change ">C(CH$_2$)$_2$" to -- >C(CH$_3$)$_2$ --;

In claim 7, column 8, line 44, delete "[>CO, >CR$^8$OR$^7$,]";

UNITED STATES PATENT AND TRADEMARK OFFICE
CERTIFICATE OF CORRECTION

PATENT NO. : 5,084,476
DATED : January 28, 1992
INVENTOR(S) : Michael Klaus and Ekkehard Weiss It is certified that error appears in the above-identified patent and that said Letters Patent is hereby corrected as shown below:

In claim 7, column 8, lines 45-46, delete "[, $-CHOR^7-CH_2-$, $-CO-CHOR^7$ or $-CHOR^7-CHOR^7$]";

In claim 10, column 9, line 18, delete "[>CO, >$CR^8OR^7$,]";

In claim 10, column 9, line 19, delete "[, $-CHOR^7-CH_2-$, $-CO-CHOR^7$ or $-CHOR^7-CHOR^7-$]";

In claim 10, column 10, line 5, change "$R^6$" to -- $R^5$ --.

Signed and Sealed this

Twenty-second Day of June, 1993

Attest:

MICHAEL K. KIRK

*Attesting Officer*  *Acting Commissioner of Patents and Trademarks*